United States Patent [19]

Whitehead

[11] Patent Number: 4,863,455
[45] Date of Patent: Sep. 5, 1989

[54] PELLET FOR ADMINISTRATION TO RUMINANTS

[75] Inventor: Derek J. Whitehead, Cheshire, England

[73] Assignee: Castex Products Limited, Poynton, England

[21] Appl. No.: 39,285

[22] Filed: Apr. 17, 1987

[30] Foreign Application Priority Data

Apr. 17, 1986 [GB] United Kingdom ............... 8609385
May 17, 1986 [GB] United Kingdom ............... 8612054
Aug. 30, 1986 [GB] United Kingdom ............... 8621039

[51] Int. Cl.$^4$ .......................................... A61M 31/00
[52] U.S. Cl. .................................. 604/890.1; 604/93; 424/438
[58] Field of Search ............... 424/438; 604/890, 892, 604/93, 890.1

[56] References Cited

U.S. PATENT DOCUMENTS 4,623,345 11/1986 Laby ...................................... 604/93

Primary Examiner—Michael Lusignan
Attorney, Agent, or Firm—Dennison, Meserole, Pollack & Scheiner

[57] ABSTRACT

A pellet for administration to ruminants to supply magnesium and other biologically active material, for example, anthelmintics or antibiotics comprises a tube of magnesium alloy 1 enclosing a core or filling 3. The core 3 typically comprises mainly iron shot as weighting material, a biologically active material if desired and an electrically conductive material such as carbon or graphite. The graphite ensures that the core 3 as a whole is conductive and provides a cathode electrically coupled with the magnesium alloy tube 1 to form a galvanic cell. Liquor in the rumen serves as an electrolyte to cause galvanic corrosion of the magnesium tube 1 to release the active material contained in the core 3. A protective coating 5 of resin is provided on the tube's exterior surface except on at least one end 4 so that the corrosion is limited to the exposed surfaces only. An alternative embodiment (FIG. 4) comprises a control magnesium alloy rod or shaft 11 around which a cylinder 13 of the electrically conductive component is pressed. The cylinder contain iron shot and graphite in similar proportions to the core 3 in the first embodiment and is also provided with a protective resin coating 12 to restrict corrosion to one or both ends of the rod 11.

15 Claims, 3 Drawing Sheets

PELLET FOR ADMINISTRATION TO RUMINANTS

British Patent 1,102,979 describes the construction of several types of pellet for supplying magnesium and other biologically active materials to ruminants and in particular cattle and sheep. The pellets are introduced into the rumeno-reticular sac via the mouth using a balling gun and remain therein for an extended period of time, typically several months, and gradually release a supply of biologically active material to the animal.

One form of pellet or bolus is tubular in shape, the tube being made from a magnesium base alloy capable of being corroded by the rumen juices. The tube may serve as a carrier for drugs such as anthelmintics, antibiotics or other biologically active material. The tube may be coated with a resin, paint, plastic, rubber or other water impermeable material on its exterior surface save for the open end of the tube. The coating protects the exterior of the tubular bolus from corrosion by the rumen juices except at the open end which is gradually corroded away. Alternatively both ends of the tube may be left open in which case corrosion proceeds from both ends simultaneously. The biologically active material is contained within the tube.

In order that the pellet should be retained by the animal it is necessary that it must have a minimum density of 2.2 gm/ml. The magnesium alloys used for these devices have a density of approximately 1.8 gm/ml and it is hence necessary to weight the tube with a dense material such as iron, in metallic form or as an oxide, silicate or other compounds. Finely divided iron shot has been widely used for weighting commercially-available magnesium boluses and is suitable for the purpose of this invention. the weighting material is mixed with the biologically active matter with or without a suitable binder and pressed to shape to form a solid core. The core may be formed in a pelleting die as a cylindrical shaped tablet or as a series of tablets and introduced into the magnesium alloy tube where they are a close fit. Alternatively the mixed ingredients are forced into the tube using a hydraulic or mechanical press to form a coherent core. This may be done in several stages and the concentration and nature of the biologically active material varied along the length of the bolus so that as corrosion of the tube proceeds the exposed core releases varying amounts of the same or different biologically active materials to the animal.

A second commercial type of such a pellet consists of a central magnesium alloy support rod which carries several segments, of plastics material, which are an interference fit on the rod. Each such segment provides a respective annular recess which contains a ring-form tablet of anthelmintic or other biologically-active material. The adjacent plastics segments abut closely to prevent ingress of liquid, and rubber sealing washers may be provided between the segments. As in the previous type of pellet the device must be weighted to provide a minimum density of about 2.2 gm/ml in order for it to be retained by the animal. In addition, it has been found that with the usual magnesium-aluminum-copper alloys which are used for these devices the magnesium alloy rod must be electrically coupled to a more electro-negative material to give the required corrosion rate. For these purposes, a steel end weight has been used, which is also carried by the magnesium alloy support rod and functions both as weight and as a cathode. In action, the magnesium rod corrodes progressively from the end remote from the weight, releasing the plastics segments and their contained tablets of drug at regular intervals. A disadvantage of this design is that the steel end weight is retained indefinitely by the animal and is undesirable in that it may eventually damage the animal and the machinery used to process the carcass.

This property can also be applied to tubular devices as previously described and it has been found that corrosion of such magnesium devices proceeds uniformly and predictably when the magnesium alloy is electrically coupled to a more-cathodic metal such as iron or copper. The rumen liquor serves as an electrolyte and sufficient chloride ion is normally present to provide a corrosive environment for the magnesium. However such a tubular device also has the disadvantage that the mass of cathodic metal would be retained by the animal with the undesirable effects previously described. Furthermore when iron shot, used as a weighting material is dispersed in the core, the resultant core is electrically non-conductive due to the presence of insulating iron oxide on the surfaces of the shot particles and the generally non conductive properties of biologically active drugs and binding materials.

It is an object of the present invention therefore to provide a pellet or bolus having an electrically conductive component galvanically coupled to a magnesium alloy component such that corrosion will proceed at a predictable and controllable rate without the disadvantage previously discussed.

With this object in view the present invention provides a pellet or bolus for administration to a ruminant by deposition in its rumeno-reticular sac characterised in that the pellet includes a magnesium alloy component and a degradable component including, dispersed therein, a biologically active material and an electrically conductive material such that the degradable component as a whole is electrically conductive and is galvanically coupled to the magnesium alloy component.

The electrically conductive material is preferably carbon powder or granules, graphite or plumbago powder. Alternatively granules or powder of any metal which is lower in the electro-chemical series than magnesium for example iron, copper, nickel or zinc can be used. Iron shot may additionally be included in the component as a weighting material.

In one embodiment of the invention is magnesium alloy component is a tube having a degradable core or filling including an electrically conductive material. The tube may be provided with a cap at one end and the degradable core or filling could be pre-formed as a plurality of discrete tablets.

In a further embodiment the magnesium alloy component is a rod which can have fins to aid cohesion around which is a cylinder of the degradable electrically conductive component.

An active material for example an anthelmintic, antibiotic or other biologically active material may be dispersed within the electrically conductive component.

In order to restrict galvanic corrosion a protective sheath, of for example, a plastic or resin, may be provided partially around the pellet such that corrosion can only proceed on exposed surfaces.

A further embodiment of the invention provides a pellet including a magnesium alloy tube, an electrically conductive core and an electrically conductive sheath surrounding the tube, the sheath preferably being a plastics material having an electrically conductive material, for example carbon, graphite, plumbago powder or metal granules or powder, dispersed therein. A development of this embodiment provides the core as a plurality of discrete tables and the sheath as a plurality of annular segments wherein the tablets axial length correspond to the sheath segments axial length. In this manner as the magnesium alloy tube corrodes a respective sheath segment and core tablet are released successively for degradation.

The invention also provides a degradable component for use in the production of or incorporation in a pellet for administration to a ruminant by deposition in its rumeno-reticular sac characterised in that the degradable component includes a biologically active material and an electrically conductive material dispersed therein such that the component as a whole is electrically conductive and galvanically coupled to a magnesium alloy component.

The preferred electrically conductive material for all the embodiments is carbon or graphite and preferably comprising from 1% to 40% by weight, ideally 4.5% for a core component containing a biologically active ingredient and weighting agent and 32% for a non weighted core.

The invention will be described further, by way of example, with reference to the accompanying drawings, in which.

Figure 1:
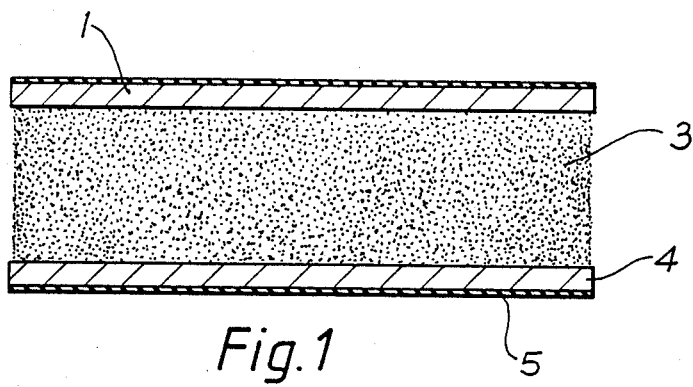
FIG. 1 is a sectional elevation illustrating a first embodiment of the bolus of the present invention.
Figure 2:
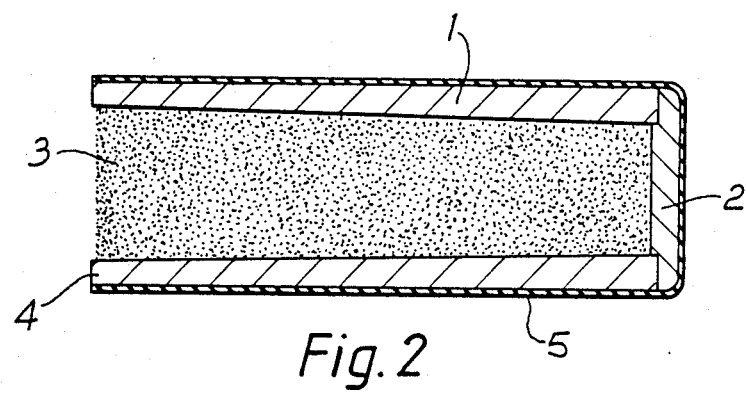
FIG. 2 is a similar view illustrating a second embodiment.

A first constructional form of the invention is illustrated in FIG. 1. In this figure, numeral 1 indicates a magnesium/aluminium alloy tube containing approximately 12% by weight of aluminium and 2% by weight of copper and 0.2% by weight manganese. The Manganese addition is made to control the iron content of the magnesium alloy and ensure that it is normally less than 0.04% by weight. The tube 1 is produced by a die casting process or alternatively by extrusion. In the former case the bore will be tapered to allow extraction of the core. If a constant rate of dissolution is required the taper may be removed by drilling. Alternatively the taper may be allowed to remain as shown in the embodiment of FIG. 2 and one end of the tube 1 closed with a plug 2 made of the same magnesium alloy as the tube. In the example shown in FIG. 2 the linear corrosion rate of the tubular bolus will decrease with time resulting in decreased release rate of the contents. After casting or extrusion the tube 1 is first given a chromate surface conversion coating by dipping in an acid chromate solution. After washing and drying the tube is coated with an epoxy resin coating 5 and this is effected by dipping in liquid resin, the resin then being cured at room temperature or an elevated temperature. This resin coating step may be repeated several times to increase the coating thickness. The resin 5 normally coats both the outside and inside of the tube 1 and the end or ends must be blanked off before dipping if the interior is not to be coated with resin. In the former case a small area of the inside of the tube 1 must be cleaned of its coating of resin 5 by drilling or abrading in order that electrical contact may be made between the tube 1 and its core 3. The tube 1 is then placed in a tubular holder attached to one of the platens of a mechanical or hydraulic press and the filling mixture is pressed in to form the core 3 at a direct load of about 10 tonnes. This may be done in one or several stages. After filling, the exterior surface of the bolus is coated with thin layer of liquid urethane resin capable of being cured at room or slightly elevated temperature. The total thickness of the resultant protective coating 5 may, for example, be about 0.125 mm but it may be, for instance, in the range from 0.05 to 0.25 mm. Prior to use, any protective coating 5 must be removed from surfaces 4. A typical mixture used for filling the bolus of 8×2.5 cm is set out below:

Benzimidazole: 11%
Graphite 100 mesh: 4.5%
Sucrose: 4.5%
S170 Iron shot: 80%

Figure 3:
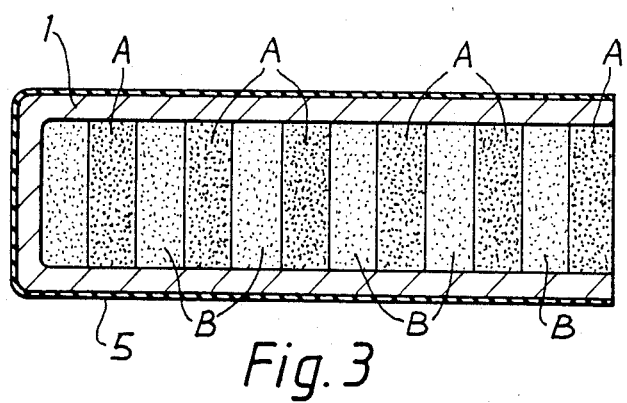
FIG. 3 is a similar view illustrating a third embodiment.

The total weight of a typical bolus for cattle is 100 gm with a density of 3.0. The life of the bolus is typically 3 to 8 months and may be controlled by varying the thickness of the magnesium alloy tube 1. FIG. 3 illustrates a variation in the construction of the bolus in which the cavity is filled with two types of graphite-loaded tablet A and B. Each tablet A, for example, may be formulated from a mixture similar to that used in forming the core 3 for the embodiment of FIGS. 1 and 2 above and contain an active drug such as an anthelmintic whilst tablets B may, for example, contain no drug or another drug. The active drug may hence only be released in pulses with intervals of time in which no drug is available to the animal or in which an alternative drug is available. It will be appreciated that the device may be scaled down in size for use with sheep.

Figure 4:
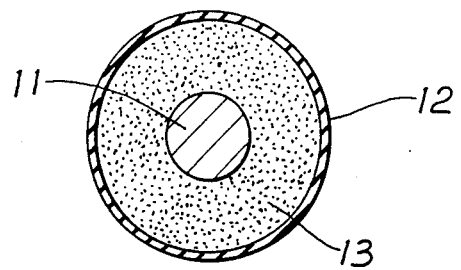
FIG. 4 is a cross-section through a fourth embodiment of the bolus of the invention.

The bolus of the invention may, if desired, incorporate a centre rod, and FIG. 4 shows one such arrangement. In this embodiment, the bolus is constructed using a magnesium alloy rod like core 11 around which a cylinder 13 of active mixture is pressed. This mixture is weighted with iron powder or shot and contains graphite to make it electrically conductive, as well as the active drug and a water soluble agent e.g. sucrose to give it some solubility in rumen liquor. The exterior surface, save for one or both ends of the bolus, are coated with a protective coating 12 of resin or lacquer, e.g. epoxy, polyester, polyurethane, acrylic or synthetic rubber. The centre rod 11 serves to maintain and augment the integrity of the bolus as it dissolves and controls the erosion rate.

Figure 5:
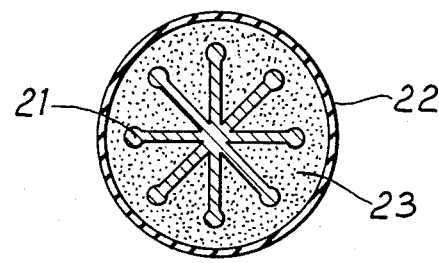
FIG. 5 is a similar view showing a fifth embodiment.

FIG. 5 shows a more complex and effective form of centre rod 21 preferably made by extrusion and around which the active mixture 23 is pressed or formed, a protective coating 22 being provided thereover in the same way as in FIG. 4. The rod 21 incorporates radial fins 24 which help to retain the moulded-on mixture 23 and add mechanical strength to the bolus.

Figure 6:
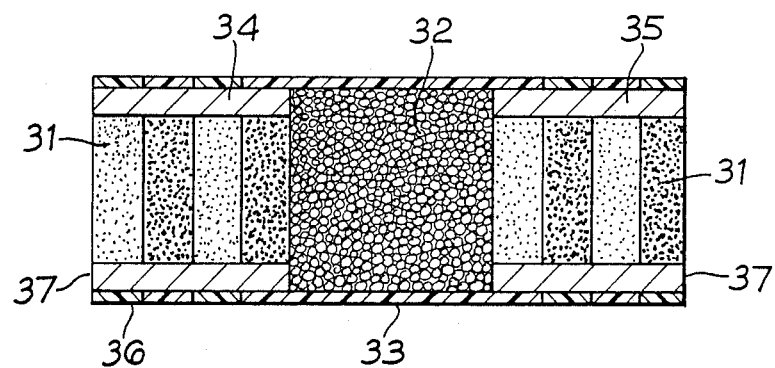
FIG. 6 is a sectional elevation illustrating a sixth embodiment of the bolus of the invention.

Referring now to FIG. 6, a sixth embodiment of the bolus according to the invention comprises a plurality of tablets 31 each containing a biologically active ingredient, for example benzimidazole, and a proportion of an electrically conductive material for example carbon.

In this embodiment the tablets do not contain any weighting material and comprise 40% benzimidazole, 28% sucrose and 32% graphite by weight. A mass of finely divided iron shot 32 is located within a plastic tube 33 which is formed containing about 40% by weight of carbon powder. The mass 32 is preferably pre-formed in a pelleting die using iron shot mixed with a small quantity of a binding agent for example molasses, dextrine or sodium silicate is inserted into the tube 33 or the mass 32 can be pressed directly into the tube 33 under pressure. The plastic tube 33 supports at either end a respective magnesium alloy tube 34, 35 each of which contains one or more tablets 31. The magnesium tubes 34, 35 are protected against attack by rumen liquor by a number of close fitting, carbon loaded plastic tires 36 disposed around the tubes' exposed surfaces. The tires 36 axial lengths correspond with those of the tablets 31 and the tyres 36 abut each other closely thus providing a liquid tight seal.

Corrosion of the tubes 34, 35 in the rumen proceeds from the exposed ends 37 of the tubes 34, 35 in a similar manner to the previously described embodiments. The magnesium alloy tubes 34, 35 provides an anode and the conductive tablets 31 and both the tires 36 and tube 33 provide cathodes thus permitting galvanic corrosion. This type of bolus offers peculiar advantages in that it is easier to manufacture the drug containing tablets as they do not contain hard particles or iron. Further as the bolus degrades progressively at its ends the density increases which aids retention of the bolus within the rumen as the ease with which objects are regurgitated increases with decreasing size and density. It is hence possible to make such a bolus with a lower initial density and yet still be sure that the bolus will be retained by the animal for the boluses lifespan.

Figure 7:
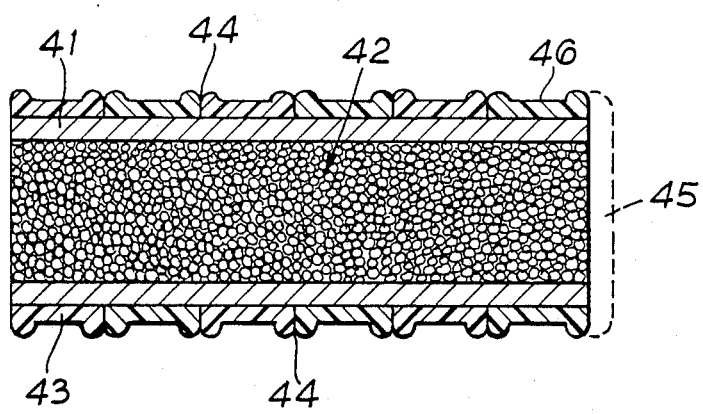
FIG. 7 is a sectional elevation illustrating a seventh embodiment of the bolus of the invention, which is a continuous release bolus.

FIG. 7 shows, in longitudinal section, a seventh embodiment of a continuous release device suitable for administration to cattle. This bolus comprises a magnesium alloy tube 41, for example about 8 cms long and 2.5 cms in diamter. This tube 41 may be diecast or extruded and is filled with an active mixture 42 similar to that used in the first and second embodiments described previously. For example:

78% S170 iron shot
10.5% sucrose
7% Benzimidazole (as active ingredient)
4.5% 300 mesh graphite the percentages being by weight.

These constituents are thoroughly mixed and pressed into the inside of the tube 41 in several stages at a direct load of about 5 tonnes. The solid core 42 thus formed is electrically conductive and capable of being eroded by the rumen contents. It is relatively dense with a density of about 4.5 gm/ml. The exterior of the tube 41 is fitted with several tyre segments 43 moulded from a conductive carbon-filled plastics material such as polypropylene or polyvinyl chloride having carbon powder dispersed therein as previously described. The internal diameter of each of the tyre segments 43 is slightly smaller than the external diameter of the magnesium alloy tube 41 and results in an interference fit between the plastics tyre 43 and magnesium tube 41. The tyres are fitted in succession using a mechanical air-operated press, giving a tight liquid-proof fit at the joints 44 between the adjacent tire segments 43. The overall density of the bolus is about 2.8 gm cc. When introduced into the rumen, the magnesium alloy tube 41 corrodes from both ends. The corrosion pattern is very uniform due to galvanic action and close proximity to the tube 41 of the conductive carbon-bearing cathodes both in the interior and at the exterior of the bolus. The corrosion rate may be controlled by varying the cross-sectional area of the magnesium tube 41. Additionally one end of the tube 41 may be closed by extending an end of the endmost segment 46 as indicated by dotted lines at 45. As corrosion of the bolus proceeds, the successive tire segments 43 fall away, limiting any tendency for the open ends of the tube 41 to become blocked by the rumen contents.

In practice, filling of the tube of such a bolus is time consuming and has the disadvantage that it is not at all easy to ensure proper filling and a homogeneous or constant consistency of the compressed filling mixture 42. Voids can arise, which can result in lack of predictability in the degradation of the filling 42 and in different degradation rates from bolus to bolus in one and the same batch. Loading of the mixture into the tube 41 prior to compressing it therein is messy, and accuracy in the amount of each load is difficult to achieve.

Figure 8:
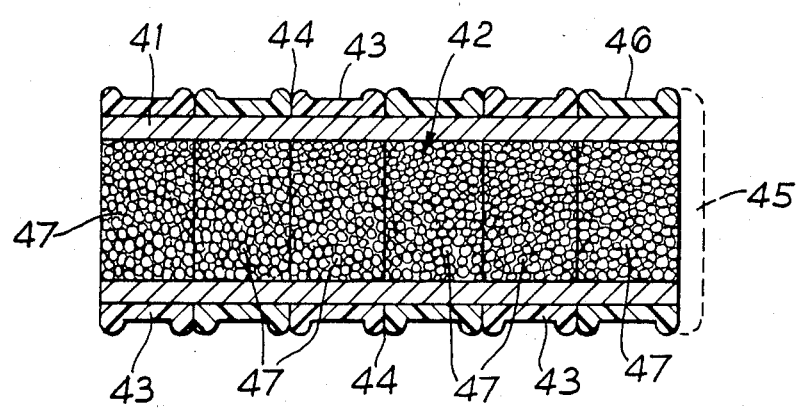
FIG. 8 is a sectional elevation of an eighth embodiment of the bolus of the invention.

These difficulties can be avoided, and certain advantages obtained by preforming the active material filling 42 into a plurality of tablets which can then be introduced into the tube 41. FIG. 8 illustrates an eighth preferred embodiment of the pellet or bolus according to the invention generally corresponding to the seventh embodiment which comprises a magnesium alloy tube 41 having an active mixture filling 42 including iron shot.

The exterior of the tube 41 is sheathed by a plurality of the tire-shaped segments 43 of a conductive plastics material such as polypropylene or polyvinyl chloride filled with conductive carbon, iron, copper, nickel or zinc in powder or particle form. These segments are an interference fit on the tube 41 being fitted successively using, for example, an air-operated mechanical press so that they abut in liquid-tight manner at their joints 44. Endmost segment 46 may, if desired, embody an end closure disc as indicated at 45, to provide for the bolus, after administration, to be degraded from one end only. The filling 42 of the bolus comprises a succession of tablets which are indicated by the reference numeral 47, and which have been prepared or pre-formed away from the tube 41, and which have been introduced successively into the tube 41, if desired with the application of pressure. As will be seen, the axial lengths of the tablets 47 correspond to the axial lengths of the sheath segments 43, so that each time a segment 43 falls away as a result of degradation of that part of the tube 41 it surrounds, any residue of the corresponding tablet 47 also falls away to ensure that the next successive tablet is exposed. This feature is not, however, essential to the invention.

This embodiment of the bolus has the advantage that it is easier to make the tablets away from the tube and introduce them into the tube (if desired or appropriate, compressing them therein) than it is to introduce a loose filling into the tube and then compress that to coherent form. The mixture can be converted into a much more compact state with less segregation of its components than occurs with the prior proposal, and the amount of the mixture used for filling the tube is much more accurately established. Furthermore, it is possible to use, in the bolus, tablets of different compositions at different positions along the tube; for instance successive tablets may contain different active ingredients and/or different amounts of such ingredients, or the tablets may be graduated in density so as to achieve a density increase with diminution of the bolus by degradation, so as to ensure retention of the bolus in the dosed animal's rumen.

I claim:

1. A pellet for administration to a ruminant by deposition in its rumeno-reticular sac, said pellet having a composite construction and comprising a first magnesium-containing component and a second degradable component containing an effective amount of a biological active material and an electrically conductive material lower in the electrochemical series than magnesium and so dispersed in said second component that said second component is electrically conductive and is galvanically coupled to said first component, said pellet including a material denser than magnesium in an amount sufficient that said pellet has a density greater than magnesium, said first and second components being degraded by galvanic action when exposed to the liquid content of the rumeno-recticular sac.

2. A pellet according to claim 1, wherein one of said components is in tubular form having a hollow core containing the other of said components, a wall surface of said hollow core providing an electrical contact face between said first and second components.

3. A pellet as claimed in claim 2 wherein the magnesium alloy component is a rod or shaft surrounded by a degradable electrically conductive cylindrical component.

4. A pellet as claimed in claim 2 wherein the magnesium alloy component is a tube having a degradable electrically conductive core or filling.

5. A pellet as claimed in claim 1, 2, or 3 wherein a protective sheath is provided partially around the pellet to restrict galvanic corrosion to exposed surfaces only.

6. A pellet as claimed in claim 5 wherein the protective sheath is electrically conductive and is galvanically coupled to the magnesium alloy component.

7. A pellet as claimed in claim 1, 2, or 3 wherein the degradable component is pre-formed as a plurality of discrete tablets.

8. A pellet as claimed in claim 6 wherein the protective sheath is formed as a plurality of annular segments.

9. A pellet as claimed in claim 6 wherein the sheath is of a plastics material having an electrically conductive material dispersed therein.

10. A pellet as claimed in claim 1, 2, or 3 wherein the dispersed electrically conductive material is carbon, graphite or plumbago powder or fibres.

11. A pellet as claimed in claims 1, 2, or 3 wherein the dispersed electrically conductive material is granules or powder of a metal lower in the electro-chemical series than magnesium.

12. A pellet as claimed in claim 11 wherein the granulated or powdered metal is iron, copper, nickel or zinc.

13. A pellet as claimed in claim 1, 2, or 3 wherein the electrically conductive component contains a quantity of iron shot as weighting material.

14. A pellet as claimed in claim 10 wherein the carbon, graphite or plumbago powder comprises from 1% to 40% by weight of the electrically conductive component.

15. A pellet as claimed in claim 7, wherein the protective sheath is formed as a plurality of annular segments, and wherein the axial lengths of the tablets correspond to the axial lengths of the annular segments.

* * * * *